United States Patent [19]

Pitesky

[11] Patent Number: 5,538,134
[45] Date of Patent: Jul. 23, 1996

[54] DISPOSABLE ALLERGEN CONTAINER AND PICK APPARATUS

[76] Inventor: Isadore Pitesky, 4001 Linden Ave., Long Beach, Calif. 90807

[21] Appl. No.: 506,486

[22] Filed: Jul. 25, 1995

[51] Int. Cl.$^6$ ............................................. A61B 10/00
[52] U.S. Cl. ........................... 206/438; 206/538; 206/559; 206/562; 128/743; 604/47
[58] Field of Search ........................ 206/438, 559, 206/562–564, 538, 569, 531; 128/743; 604/46–49, 181, 191; 220/523, 526; 53/400

[56] References Cited

U.S. PATENT DOCUMENTS

| | | | |
|---|---|---|---|
| 1,815,568 | 7/1931 | Jacqmein | 206/315.11 |
| 1,869,717 | 8/1932 | Silver | 118/503 |
| 2,522,309 | 9/1950 | Simon | 128/743 |
| 2,610,430 | 9/1952 | Neiman | 43/57.5 |
| 2,860,768 | 11/1958 | Smither | 206/46 |
| 2,861,682 | 11/1958 | Hatcher | 206/75 |
| 3,289,670 | 12/1966 | Krug et al. | 604/47 |
| 3,435,946 | 4/1969 | Sobek et al. | 206/46 |
| 3,502,224 | 3/1970 | Heinze | 211/69.8 |
| 3,921,804 | 11/1975 | Tester | 206/531 |
| 4,237,906 | 12/1980 | Havstad et al. | 128/743 |
| 4,265,362 | 5/1981 | Suonvieri | 211/60 R |
| 4,292,979 | 10/1981 | Inglefield et al. | 128/743 |
| 4,304,241 | 12/1981 | Brennan | 128/743 |
| 4,657,138 | 4/1987 | Watson | 206/366 |
| 4,769,941 | 9/1988 | Schmidt | 43/57.1 |
| 4,802,493 | 2/1989 | Maganias | 128/743 |
| 4,826,003 | 5/1989 | Levy | 206/45.31 |
| 4,863,023 | 9/1989 | Payne et al. | 206/364 |
| 4,917,235 | 4/1990 | Feiler | 206/6.1 |
| 5,027,972 | 7/1991 | Bartholomew | 220/526 |
| 5,154,181 | 10/1992 | Fishman | 128/743 |

*Primary Examiner*—Paul T. Sewell
*Assistant Examiner*—Luan K. Bui
*Attorney, Agent, or Firm*—Fulwider Patton Lee & Utecht

[57] ABSTRACT

A disposable allergen container apparatus for individual application to a patient of a plurality of allergens including a tray, a formed thermoplastic cover and an applicator. The tray includes a horizontal top web formed with a plurality of open top, vertically recessed wells arranged in predetermined spaced relationship and configured with respective bottom sinks configured to receive and store a supply of respective allergens therein. The cover includes a plate for overlying the web and is formed with a plurality of nesting rings arranged in the predetermined spaced relationship for centering over the respective sinks and spaced a predetermined distance therefrom. The applicator includes a finger grip knob formed with a downwardly facing nesting shoulder for nesting on the respective nesting rings and further includes an elongated pick formed on its bottom end with a penetration point of sufficient length to, when the nesting shoulder is nested on one of the respective nesting rings, project into the respective sink to be immersed in the respective allergen.

21 Claims, 2 Drawing Sheets

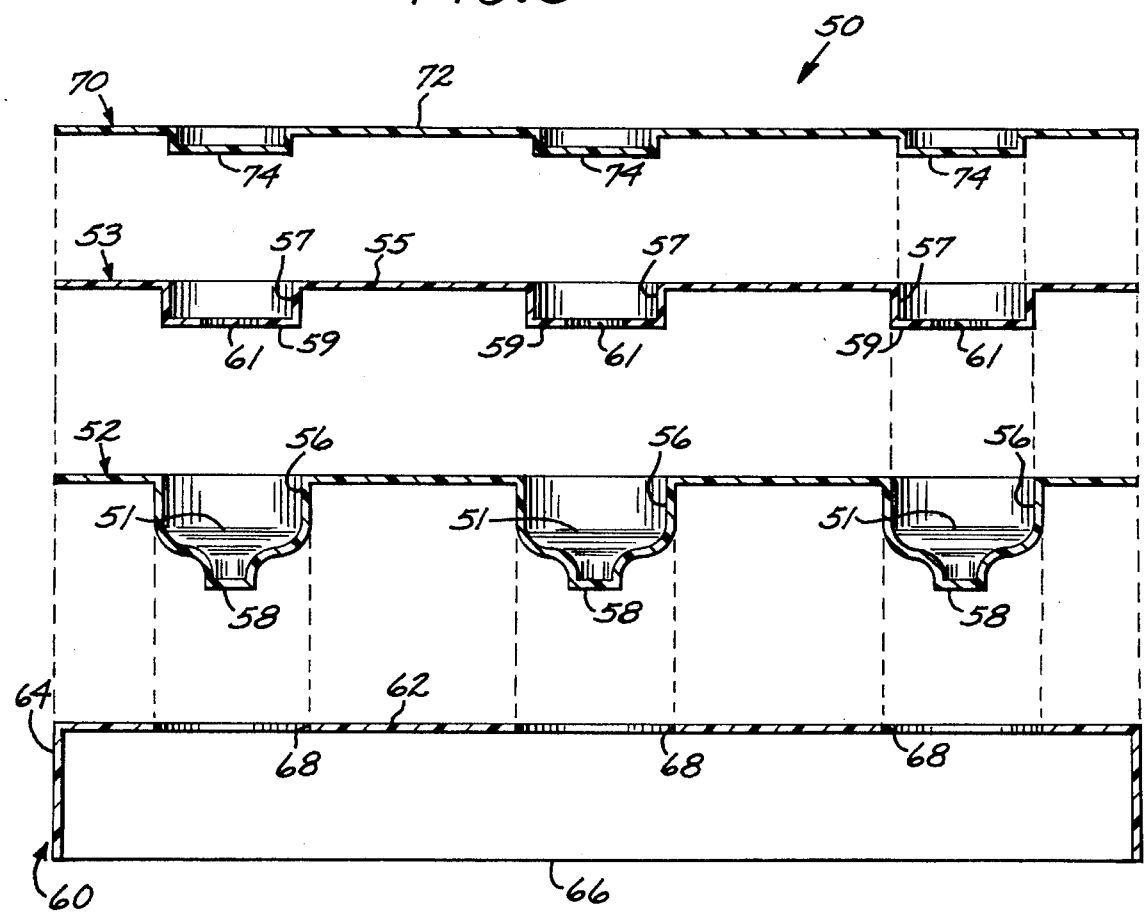

DISPOSABLE ALLERGEN CONTAINER AND PICK APPARATUS

BACKGROUND OF THE INVENTION

1. Field of the Invention

The present invention relates to allergy testing and, more particularly, to a device that allows for containment of a plurality of allergens and for the individual application of such allergens for testing a patient's reaction thereto.

2. Description of the Prior Art

Allergy testing involves subjecting a patient to a wide variety of different allergens to determine which allergens cause allergic reactions in the patient. Such testing requires that the respective allergens be applied beneath the surface of the patient's skin. One conventional method is to individually place a drop of allergen on the patient's skin and then prick the contacted skin so that the allergen will be delivered under the patient's skin. In another method, an allergen is deposited on a pick at the end of an applicator and the patient's skin pricked to deliver the allergen beneath the surface.

Applicator picks of this type have been proposed arrayed on a sprue to be broken individually therefrom along respective break lines such that the picks may be individually removed so the respective pointed tips may be pressed against the epidermis on which allergen has been previously deposited. It has also been proposed to package a number of individual picks in a container to be removed individually for use. Various tray devices have been proposed for use with such picks.

Other individual picks have been proposed which incorporate a tiny cup shaped plastic button opening to one side and having a sharp pick projecting centrally therefrom so that drops of selected allergens may be dropped into different ones of such buttons and the buttons then applied to the patient's skin to penetrate the skin surface with the central pick. A device of this type has been advertised by Combion Systems Incorporated, 1712 Clubhouse Road, Suite 102, Reston Va. 22090 as disclosed in U.S. Pat. No. 4,473,083.

Multiple allergen applicator devices have been developed including a multitude of applicator picks arrayed in predetermined spaced relations so that in one application, such multitude of allergens are delivered to the patient simultaneously. One such multiple allergy testing apparatus is disclosed in U.S. Pat. No. 4,292,979 and includes a multitude of applicator picks fixedly attached to a hand held applicator. The applicator picks are arranged for overlying a support base having a plurality of apertures formed therein for removable receipt of disposable vials containing allergens. In operation, the hand held applicator is positioned over the vials to submerse the respective picks in such allergens to wet the picks for subsequent application to the patient. In U.S. Pat. No. 5,154,181, another hand held allergy testing apparatus is disclosed having a multitude of applicator needles fixedly attached by means of machine screws to a movable applicator member to inject a preset number of allergens under a patient's skin.

The aforementioned multiple applicator devices incorporate a multitude of components requiring time consuming assembly, including the individual attachment of the respective picks or needles to the hand held applicator resulting in increased cost of production and increased cost of the testing apparatus as a whole.

With economy in mind, it has been found desirable to provide allergen application devices that are so inexpensive to manufacture it would be practical to dispose of them after a single use. By way of example, one such disposable applicator formed with a multitude of ganged together applicator picks is sold by Lincoln Diagnostics Inc., Decater, Ill. under the trade designation "MULTI-TEST" as shown at 30 USPQ2d 1817 and at 1821 (U.S. TTAB), U.S. Pat. No. 3,556,080. The multiple applicator devices shown are in the form of plastic frames formed with laterally disposed legs terminating in spaced apart feet defining respective penetration points disposed in a common plane for receipt of respective allergens to be simultaneously applied to a patient.

Although such multiple allergen applicators have been found acceptable for their intended purpose, the fixed number of applicator picks subject the patient to a fixed number OF skin pricks irrespective of whether or not the testing by a full complement of allergens is dictated. In addition, some clinicians prefer to use a single applicator device so the location on the patient's skin can be selective.

One such application is in the form of a portable tray incorporating upwardly opening wells spaced thereabout for receipt of tubular shaped vial tubes containing the respective allergens. The vial tubes are configured for receipt of the picks of the individual applicators to be submersed in the respective allergens for subsequent application to the patient. A device of this type is shown in my U.S. Pat. No. 4,237,906 and, although such device has been very effective in use, the costs associated with the production and manufacture thereof are substantial.

Hence those skilled in the art have found a need for a disposable multiple allergen container device that allows for individual application of such multitude of allergens under a patient's skin while allowing for practical disposal of such device after use. In addition, there continues to be a need for a container device which limits the waste materials created by the use thereof. Moreover, the device should incorporate a minimum number of relatively inexpensive components to minimize manufacturing costs and decrease assembly time. The instant invention addresses such needs.

SUMMARY OF THE INVENTION

Briefly, and in general terms, the present invention is directed to a multiple allergen container apparatus for use with a hand held single allergen applicator for applying to a patient a plurality of allergens.

In accordance with the invention, the allergen container apparatus includes a well tray and a cover for overlying such tray. The well tray is integrally formed of thermoplastic to define a horizontal top web formed with a plurality of open top, vertically recessed wells arranged in predetermined spaced relationship and configured with respective bottom sinks. The wells are configured to receive and store a supply of the respective allergens therein.

The cover is likewise integrally formed of thermoplastic to be configured with a plate for overlying the web of the well tray and is formed with a plurality of nesting rings arranged in the predetermined spaced relationship to be centered over the respective sinks, the rings being spaced a predetermined distance from the respective sinks.

The hand held applicator is of the type including a finger grip knob formed with a downwardly facing nesting shoulder for nesting on the respective rings of the cover and is further formed with a pick depending from such nesting shoulder and formed on its bottom end with a penetration point. The pick is of sufficient length to, when the nesting shoulder is nested on one of the respective nesting rings, project into the respective sink to immerse the penetration point within the respective allergen contained therein.

In a more detailed aspect, the pick is configured at its distal tip with a predetermined cross section and the respective wells at their bottom ends convergingly taper downwardly and inwardly to form the respective sinks having a reduced-in-cross section. When the nesting shoulder of the applicator is nested on one of the nesting rings, the distal tip of the pick is received in close fitting relationship within the reduced-in-cross section sink.

In a more particular aspect, the plate of the cover is formed with a plurality of integrally formed vertically recessed sockets being circular shaped in cross section and arranged in the predetermined spaced relationship in conformity with the wells of the well tray and formed on their respective lower ends with the nesting rings.

In a further aspect of the invention, the open top ends of the respective sockets are formed in a predetermined configuration, and the container apparatus further includes a lid formed with a horizontal sheet integrally formed with a plurality of downwardly projecting plugs arranged in the predetermined spaced relationship configured to be removably received in stopping relationship within the open top ends of the respective sockets.

In one aspect of the invention, the horizontal top web of well tray is formed with an integral peripheral wall projecting downwardly around the entire periphery of the web and terminating in a bottom support edge.

In an alternative aspect of the invention, a base is provided and is formed with an upstanding peripheral wall terminating in a bottom support edge and formed with a horizontal top wall formed with a plurality of well holes arranged in the predetermined spaced relationship. As such, the well tray is configured to be positioned on the plate of the cover for receipt of the respective downwardly projecting wells within the respective well holes of the base.

The apparatus of the present invention may be manufactured by first forming the tray from a sheet of thermoplastic then forming the cover and affixing the two together.

Other features and advantages of the invention will become apparent from the following detailed description taken in conjunction with the accompanying drawings, which illustrate by way of example, the features of the invention.

BRIEF DESCRIPTION OF THE DRAWINGS

FIG. 3 is a cross sectional view, similar to that shown in FIG. 2, of an alternative embodiment of the disposable allergen container apparatus.

DETAILED DESCRIPTION OF THE PREFERRED EMBODIMENT

Figure 1:
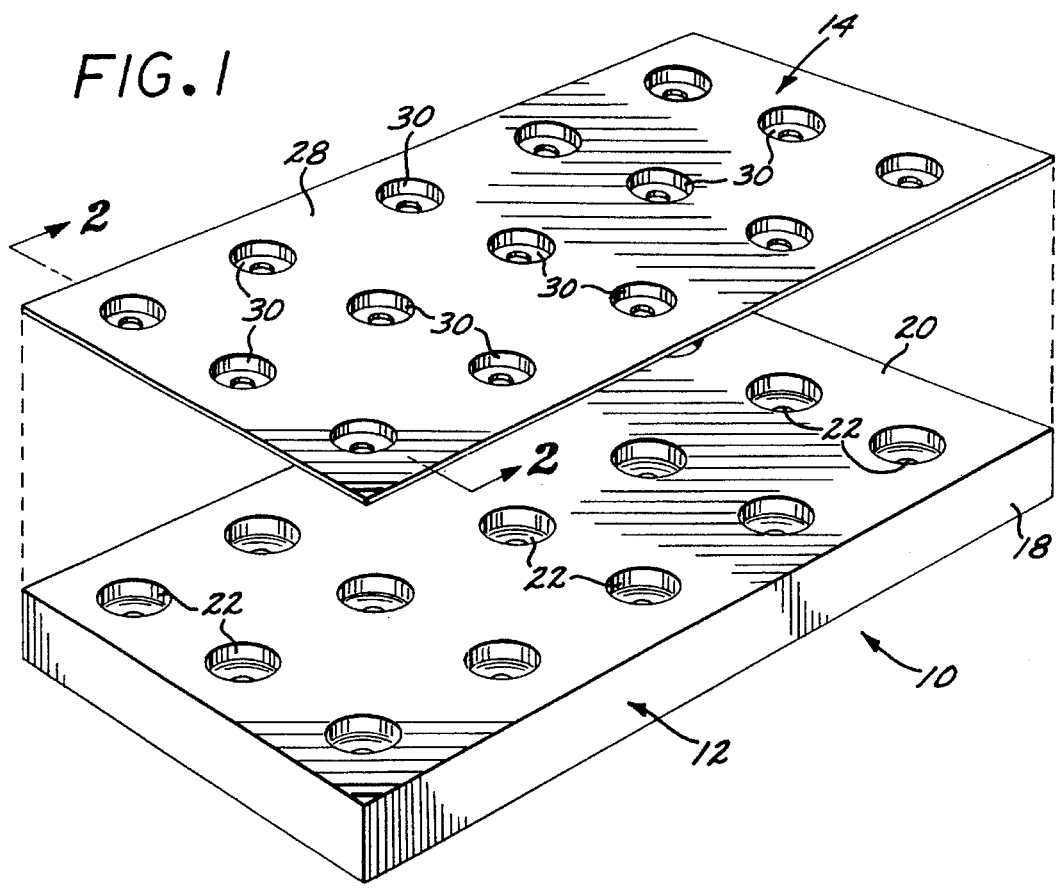
FIG. 1 is a perspective view of a disposable allergen container apparatus embodying the present invention.

In the following detailed description, like reference numerals will be used to refer to like or corresponding elements in the different figures of the drawings. Referring to the FIGURES, the invention is embodied in a convenient, disposable multiple allergen container 10 for containing and storing a plurality of allergen testing materials and configured for use with a hand held allergen applicator 16 for facilitating convenient application of such allergens individually to the patient.

Briefly, and in general terms, the container apparatus 10 includes a thermoplastic formed well tray 12 overlaid by a cover 14 for a hand held allergen applicator 16 (FIG. 2) including an applicator pick 17 for individually administering the respective allergens under the skin of the patient. The allergen container apparatus 10 provides for ease in wetting of the applicator pick with the respective allergen testing materials and also provides for efficient use of such allergens to thereby reduce testing material costs while limiting the amount of residual, unused allergen. In addition, the container apparatus and hand held applicator are formed of relatively inexpensive materials and include a minimum number of components for minimizing production costs.

Figure 2:
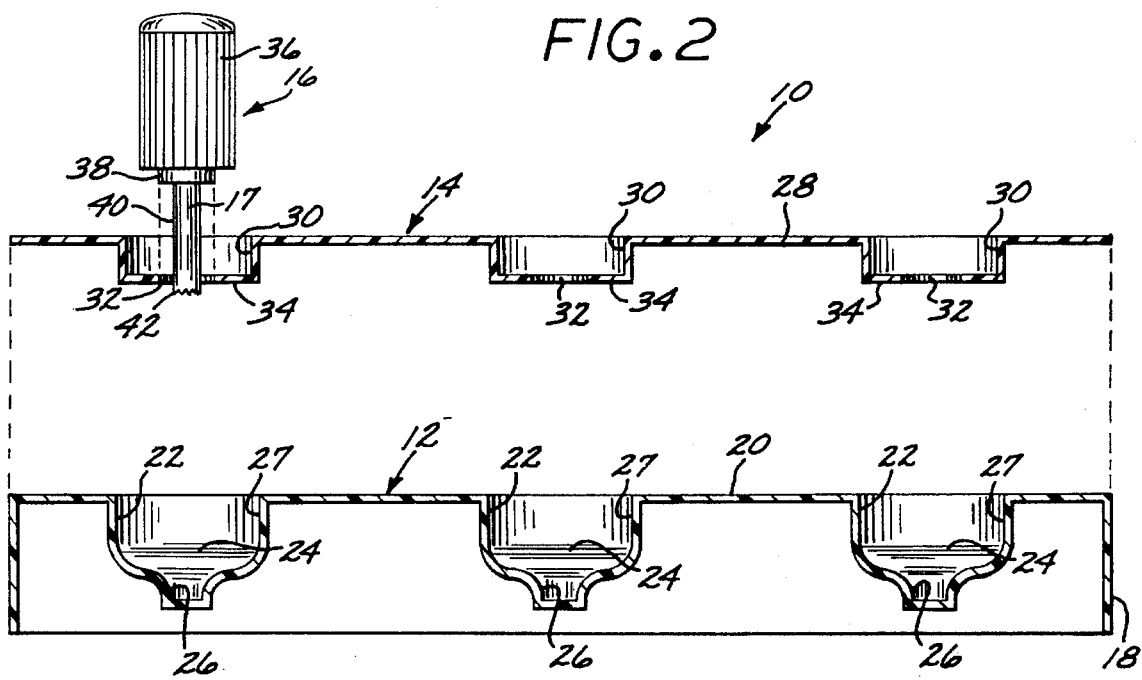
FIG. 2 is a cross sectional view, in enlarged scale, taken along the line 2—2 of FIG. 1.

Referring to FIGS. 1 and 2, the well tray 12, in one embodiment, is generally formed by a hollow downwardly opening integral rectangular box having an upstanding vertical peripheral wall 18, the bottom edge thereof terminating in a horizontal plane to define a bottom support. The tray is formed with a horizontal web 20 formed integrally with a plurality of recessed, open top cylindrical allergen wells, generally designated 22. The wells are formed in predetermined spaced apart relationship for receipt in each of a supply of different liquid allergens 24 (FIG. 2). The wells, for purposes of illustration, are spaced apart in three adjacent parallel rows, five wells to a row, and configured to receive in their respective open top ends, the allergen applicator pick 17 of the hand held applicator 16 described in more detail below.

In a preferred construction, the well tray 12 is constructed of a lightweight, thin walled, thermoplastic material such as PET-G or polycarbonate, and may be integrally molded over a forming mold using vacuum forming processes well known by those skilled in the art. As such, the peripheral wall 16 of the well tray 12 may be formed with a slight downwardly diverging draft and the side walls of the respective wells 20 may be formed with a slight converging downwardly draft to facilitate removal of the formed tray from the mold. The tray may be on the order of ⅝ inch high, 4 inches wide, and 7 inches long.

With particular reference to FIG. 2, the wells 22 of the tray 12 are generally cylindrical having cylindrical open top ends to define respective necks 27 of predetermined diameter. The bottom ends of the respective wells convergingly taper in a smooth curved manner radially inwardly and then downwardly to form respective reduced-in-diameter cylindrical collection basins defining sinks 26 having respective flat bottom surfaces. The respective wells are formed to have uniform, predetermined depths such that the bottom surface of the collection sinks terminate in a common horizontal plane.

In general, the cover 14 includes a horizontal, rectangular flat sheet defining a plate 28 integrally formed with the plurality of vertically recessed sockets 30 having open top ends and being circular shaped in cross section and arranged in predetermined spaced relationship complementary to that of the respective wells 22 of the well tray 12. The cover 14 is preferably constructed of thermoplastic materials such as PET-G or polystyrene, and may be integrally molded over a forming mold using vacuum forming processes or the like. The sockets 30 are of a predetermined depth and are formed with respective bottom walls defining respective nesting rings 34 configured with respective central centering bores defining openings 32 of a selected diameter. The cover 14 is sized and configured for alignment over the well tray 12 to be positioned in complementary overlying relationship thereon to receive the respective downwardly recessed sockets 30 in close fit relationship within the respective necks 27 of the wells 22.

With continued reference to FIG. 2, the hand held allergen applicator 16 includes a grooved or knurled enlarged in diameter cylindrical finger grip 36 to be grasped by the fingers of a clinician. The bottom end of the finger grip 36 is stepped down to form a downwardly facing annular nesting ring 34 and a reduced in diameter downwardly projecting cylindrical collar 38. Projecting centrally downwardly from such collar is an integrally formed stem 40. The collar 38 is of a cross sectional diameter sized for receipt in slip fit relationship with the respective bores 32. It is to be appreciated that the grip 36 is configured for convenient grasping and handling to direct the applicator pick 17 to the desired location of the patient's skin and for ease in applying the requisite compressive force thereto to break the surface of such skin. In the preferred configuration, the hand held applicator 36 is constructed of thermoplastic materials such as polypropylene, acetal or polycarbonate and formed, for instance, by injection molding processes well known by those skilled in the art.

The elongated stem 40 terminates at its bottom end in a penetration point 42 formed with sharp jagged edges to pierce the skin surface upon application thereto. The stem 40 of the applicator pick 17 is generally slender and cylindrical, although its particular shape and cross sectional geometry may vary. It is to be appreciated that the stem 40 of the applicator pick 17 has a predetermined length such that, when the nesting shoulder 37 nests on the resting rings 34, the penetration point 42 will be immersed in the respective allergen 24 contained in the respective sink 26.

Referring now to FIG. 3, an alterative embodiment of the disposable container apparatus, generally designated at 50, includes, generally, a well tray 52, cover 53, base 60 and lid 70. The well tray 52 is configured to overly the base 60, the cover 53 is configured to overly the tray 52, and the lid 70 is configured to overly the cover 53. The base, well tray, cover and lid may be each integrally formed of thermoplastic materials.

The well tray 52 is formed similarly as described above including the horizontal web 54 formed integrally with the respective recessed wells 56 having the reduced-in-diameter sinks 58 formed at the respective bottom ends thereof and into which a supply of respective allergens 51 may be received therein. It is to be appreciated, however, that in this embodiment the well tray 52 does not include a formed peripheral upstanding wall and is configured for removably overlying the support base 60.

The cover 53, as described above, includes a horizontal flat plate 55 integrally formed with the plurality of vertically recessed sockets 57 of a predetermined depth and formed on their respective lower ends with respective nesting rings 59 having respective central openings 61 therethrough.

The base 60 is configured for supporting the well tray thereon and includes a horizontal top wall 62 formed integrally with a downwardly projecting peripheral side wall 64 terminating in a bottom support edge 66. The base may be constructed of thermoplastic materials such as PET-G or polycarbonate and formed using vacuum molding processes or the like. As such, the side wall 64 may be formed with a slight draft for removing such base from the mold. The horizontal top wall 62 of the base is formed with a plurality of well holes 68 arranged in the predetermined spaced relations configured such that the well tray 50 may be positioned on the base 60 for receipt of the respective downwardly projecting wells 56 within the respective well holes 68. It is to be appreciated that the base is constructed for more permanent use, although may be disposable as well.

With continued reference to FIG. 3, the lid 70 includes a rectangular horizontal top sheet 72 integrally formed with a plurality of downwardly depressed cylindrical plugs 74 arranged in complementary predetermined spaced relations to the respective sockets 57 of the cover 53 and configured to be removably received in stopping relationship therein. The lid 70 may also be formed of thermoplastic such as PET-G or polystyrene, and formed using vacuum molding processes or the like. The lid is configured to be releasably removed from the cover 53 to access the respective allergens 51 contained in the wells 56 of the well tray 52.

Returning back to FIGS. 1 and 2, it is to be appreciated that the disposable allergen container apparatus 10 is configured to be conveniently packaged for subsequent sale and distribution to clinicians to be kept on hand for performing allergy tests. The well tray 12, cover 14 and lid 50 may be fabricated as described above and then sterilized using techniques well known to those skilled in the art. Thereafter, suitable volumes of commonly used pre-selected respective allergens 24 are delivered into the respective wells 22. Then, the cover 14 may be positioned over the well tray to align the respective sockets 30 downwardly over the respective wells 22 and the cover advanced downwardly thereon to snugly receive within the top ends of the wells the respective sockets and urged downwardly thereon far enough to engage the cover plate 28 with the horizontal web 20 of the well tray 12.

A lid 70 of the configuration shown in FIG. 3 may then be similarly positioned over the cover 14 to align the respective plugs 74 downwardly over the open top ends of the respective sockets 30 to be snugly received therein. As such, the plugs 74 stop the wells 22 to contain the respective allergens therein for storage and shipment. It can be appreciated that the full assembly of the container apparatus 10 is completed in a minimum number of steps.

Furthermore, it is to be appreciated that the respective wells 22 may be filled with different selected combinations of allergens 24 for use in performing tests for different allergies. As such, the clinician may select a particular allergen container apparatus 10 containing a certain combination of allergens to be administered to patients exhibiting particular allergic symptoms.

Thereafter, the applicator 16 and assembled allergen container 10 may be packaged as by, for instance, vacuum sealing in a protective sterilized plastic cover for packaging and storage. It is to be appreciated that the hand held applicator picks 16 are packaged separately from the container 10.

In the alternate embodiment represented in FIG. 3, the well tray 52 may be positioned over the base 60 in overlying relationship and then packaged together with the cover 53 and lid 70.

In use, the allergen container apparatus 10 of the present invention may be stored in the clinician's office for convenient and rapid retrieval ready for immediate use. To perform an allergy testing procedure, the clinician may remove the container 10 from the sterile packaging and unpackage the applicator 16. The clinician can then remove the lid 70 from the cover 14 to access the wells 22 containing the respective allergens 24 therein. Then, the clinician may conveniently grasp the finger grip 36 of the applicator 16 with his or her fingers and align the applicator pick 17 over a selected allergen well 22 centered over the central opening 32 of the respective socket nesting ring 34. The clinician can then direct the applicator 16 downwardly to insert the pick 17 through the selected central opening 32 to align the collar 38 in such opening and the bottom shoulder 37 on the respective nesting ring 34 thereby positioning the distal end thereof and the penetration point 42 within the respective allergen 24 contained in the sink 26 of such well.

With the shoulder 37 resting on the respective nesting ring 34 of the selected socket 30, it is to be appreciated that the length of the stem 40 of the applicator pick 17 and the depth of the collection sinks 26 at the bottom of the respective wells 22 relative to the nesting rings are so configured as to dispose the distal end of the applicator stem 40 and the penetration point 42 thereof in close fitting relationship coaxially within the collection sink 26 while maintaining the point 42 in close spaced relationship with, but spaced slightly from, the bottom surface of the sink. This positions the point 42 such that it will be submersed in the allergen in such sink, even as the volume of such allergens approach depletion while preventing direct engagement with the respective walls of such sinks to thereby maintain the integrity of the sharp jagged edges of such points.

The clinician may then grasp the finger grip 36 of the applicator 16 to withdraw such applicator 16 from the socket 30 to withdraw the applicator pick 17 from the respective sink 26. As the pick 17 is withdrawn from the sink 26, a drop of the respective allergen 24 forms about the point 42. The clinician may then direct the applicator 16 to position the tip 42 at a selected location on the patient's skin and apply the requisite compressive force to break the skin and apply the allergen thereunder. It is to be appreciated that the clinician may twist the applicator 16 while applying such compressive force to the skin causing the jagged point 42 to pierce the skin more effectively. The application of the allergen to the patient is thereby completed in a very short period of time, perhaps in only a matter of seconds.

After the clinician has completed the allergen application procedure, he or she will then dispose of the respective applicators 16 using known techniques. Thereafter, new sterile applicators 16 may be introduced to selected sockets 30 for subsequent use with the respective applicator points 42 submersed in the respective allergens 24. It is to be appreciated that the applicators 16 are thus in position for conveniently applying allergens to the next patient. As such, when the clinician then desires to perform additional allergen testing on this or another patient, he or she may retrieve the applicators to repeat the process with the applicator picks 17 having the allergens pre-applied to the penetration points 42. The clinician is therefore relieved of the time consuming and tedious task of applying allergen solutions individually to the picks.

As application of the selected allergens 24 is repeated to further patients, the volume of the allergens contained in the respective wells 22 will be gradually depleted. It is to be appreciated that the unique shape of the collection sinks 26 at the bottom of the respective wells 22 provide for an efficient use of the respective allergens. As picks 17 are reintroduced into the wells 22, the close fitting relationship between the distal end of the pick in the collection sinks 26 will cause the residual allergens to be contained in a vertical column in the respective sinks 26 to surround such distal end such that a sufficient volume of allergen adheres to the pick for subsequent application to the patient. As such, the total volume of expensive allergens to be packaged in the wells 22 of the allergen container apparatus 10 is minimized, reducing costs to the end user while, even as the supply of allergens is being depleted, providing a sufficient volume of the respective allergens pooled in such sinks to be applied to the applicator point 42. In addition, the amount of waste allergen material to be disposed at the completion of the task is limited. When the supply of allergens has been depleted, the user may merely discard the relatively inexpensive container apparatus 10 for disposal with other medical waste material.

From the foregoing, it will be appreciated that the allergen container apparatus of the present invention provides a convenient disposable device for use with a single allergen applicator device that provides for quick and easy individual application of a plurality of allergens to a patient. The container apparatus and applicator may be formed of relatively inexpensive thermoplastic materials allowing for convenient disposal thereof after use. The container apparatus and applicator incorporate few components and are formed of relatively inexpensive materials and are of simple construction to provide for cost effective and rapid manufacture. The apparatus provides for conveniently pre-wetting the allergen applicator pick to eliminate the step of applying respective allergens to each individual respective applicator pick immediately before performing an allergy test resulting in time savings as well as conservation of expensive allergen testing materials. In addition, the container apparatus provides for efficient use of allergen testing materials thereby further reducing costs while limiting the amount of waste allergen material which must be disposed of.

While particular forms of the invention have been illustrated and described, it will also be apparent that various modifications can be made without departing from the spirit and scope of the invention. Accordingly, it is not intended that the invention be limited, except as by the appended claims.

What is claimed is:

1. A disposable allergen container apparatus:
   a formed thermoplastic tray including a horizontal top web formed integrally with a plurality of open top, downwardly recessed wells arranged in predetermined spaced relationship and configured at their respective top ends with necks and at their respective bottom ends with bottom walls;
   a formed thermoplastic cover including a plate overlying said web formed integrally with a plurality of nesting rings arranged in said predetermined spaced relationship to form central bores centered over the respective said wells, said rings being spaced a predetermined distance from the respective said bottom walls;
   at least one applicator having an upstanding handle and formed with downwardly facing annular shoulder and a concentrically disposed pick projecting downwardly therefrom to define a tip arranged to, when said pick is received in one of said bores of one of said rings with shoulder nested on said ring, be disposed adjacent the said bottom wall of the said well; and
   a cover for covering the respective said necks.

2. The apparatus of claim 1 wherein:
   said horizontal top web of said tray is formed with an integral peripheral wall projecting downwardly around the entire periphery of said web terminating in a bottom support edge.

3. The apparatus of claim 1 further including:
   a base formed with an upstanding peripheral wall terminating in a bottom support edge and formed with a horizontal top wall formed with a plurality of well holes arranged in said predetermined spaced relations, said tray configured to be positioned on said plate for receipt of the respective said wells within the respective said well holes.

4. The apparatus of claim 1 wherein:

said plate is formed with a plurality of integrally formed downwardly recessed circular sockets arranged in said predetermined spaced relationship configured to project downwardly into the respective said sockets and formed on their respective lower ends with the respective said nesting rings.

5. The apparatus of claim 4 wherein:

the respective said sockets are formed at their respective top ends with necks of a predetermined configuration, and said apparatus further includes:

a lid formed with a horizontal sheet integrally formed with a plurality of downwardly projecting plugs arranged in said predetermined spaced relations configured to be removably received in stopping relationship within the respective said necks.

6. The apparatus of claim 1 for use with a pick configured at its distal tip with a predetermined cross section and wherein:

the respective said wells are formed at their respective bottom ends to convergingly taper downwardly and inwardly to form respective sinks with a cross section to, when said shoulder of said applicator is nested on a selected one of said nesting rings, receive in close fit relationship said tip.

7. The apparatus of claim 1 wherein:

said tray is formed with said web, and wells integral with one another.

8. The apparatus of claim 1 wherein:

said tray is configured with said wells arranged in three rows numbering substantially five in each row.

9. The apparatus of claim 2 wherein:

said tray is configured with said peripheral wall about ⅝ inch high.

10. The apparatus of claim 1 wherein:

said wells are cylindrically shaped and are formed in their respective bottom walls with reduced-in-diameter downwardly recessed sinks configured to, when said applicator is positioned with said shoulder on a respective said ring, receive said tip in close fitting radial relationship.

11. The apparatus of claim 1 that includes:

filling the respective said wells with selected allergens.

12. A disposable allergen container apparatus comprising:

a formed thermoplastic tray including a horizontal top web formed with a plurality of open top, vertically recessed cylindrical wells arranged in predetermined spaced relationship and configured with respective bottom sinks;

a formed thermoplastic cover including a plate overlying said web and formed with a plurality of integrally formed downwardly recessed cylindrical sockets arranged in said predetermined spaced relationship and formed on their respective lower ends with respective nesting rings to be centered over the respective said sinks and spaced a predetermined distance therefrom; and an applicator including an upstanding finger grip knob formed on its bottom end with a downwardly facing annular nesting shoulder sized for receipt within selected ones of the respective said sockets and configured for nesting on the respective said rings, said applicator including a pick formed concentric with said shoulder and projecting downwardly a selected distance to form a tip configured to, when said nesting shoulder is nested on a selected one of the respective said nesting rings, project downwardly into the respective said sink.

13. The apparatus of claim 12 wherein:

said horizontal top web of said tray is formed with an integral peripheral wall projecting downwardly around the entire periphery of said web terminating in a bottom support edge.

14. The apparatus of claim 12 further including:

a base formed with an upstanding peripheral wall terminating in a bottom support edge and formed with a horizontal top wall formed with a plurality of well holes arranged in said predetermined spaced relations, said tray configured to be positioned on said plate for receipt of the respective said downwardly projecting wells within the respective said well holes.

15. The apparatus of claim 12 wherein:

the respective said sockets are formed at their respective top ends with necks of a predetermined configuration, and said apparatus further includes:

a lid formed with a horizontal sheet integrally formed with a plurality of downwardly projecting plugs arranged in said predetermined spaced relations configured to be removably received in stopping relationship within the respective said necks.

16. The apparatus of claim 12 wherein:

said pick is configured at its distal tip with a predetermined cross section; and the respective said wells at their bottom ends convergingly taper downwardly and inwardly to form the respective said sinks with a cross section to, when said nesting shoulder of said applicator is nested on a selected one of said nesting rings, receive said tip in close fit relationship.

17. The apparatus of claim 12 wherein:

said tray is formed with said web, and wells integral with one another.

18. The apparatus of claim 12 wherein:

said tray is configured with said wells arranged in three rows numbering substantially five in each row.

19. The apparatus of claim 13 wherein:

said tray is configured with said peripheral wall about ⅝ inch high.

20. A method of making a disposable allergen container apparatus comprising the steps of:

thermally forming a plastic tray from a sheet of thermoplastic to form a horizontal top web formed with a plurality of open top, downwardly recessed wells arranged in predetermined spaced relationship and configured with bottom walls;

thermally forming a thermoplastic cover to include a plate for overlying said web and a plurality of integral rings defining central openings and, arranged in said predetermined relationship;

placing said cover over said top web with the said nesting rings centered over the respective said wells;

filling said wells with selected allergens;

placing a lid over said wells to hold said allergens in place;

selecting at least one applicator of the type including an upstanding handle formed with a downwardly facing annular shoulder for, when said lid is removed, nesting on selected ones of said rings with a concentrically dispersed pick projecting downwardly to terminate in a tip having a plurality of sharp edges disposed in the allergens within the well dispersed beneath said selected ring.

21. The method as set forth in claim 20 that includes:

filling said wells with said selected allergens;

selecting a lid to sealingly fit over said cover;

placing said lid over said cover in sealing relationship over said openings to seal said allergens in the respective said wells.

* * * * *